United States Patent
Hernandez-Rivera et al.

(10) Patent No.: US 8,932,384 B1
(45) Date of Patent: Jan. 13, 2015

(54) SURFACE ENHANCED RAMAN SPECTROSCOPY GOLD NANORODS SUBSTRATES FOR DETECTION OF 2,4,6-TRINITROTOULENE AND 3,5-DINITRO-4-METHYLBENZOIC ACID EXPLOSIVES

(75) Inventors: Samuel P. Hernandez-Rivera, Mayaguez, PR (US); Oliva M. Primera-Pedrozo, San Juan, PR (US); Ana M. Chamoun-Emanuelli, Mayaguez, PR (US); Wilmarie Medina-Ramos, Moca, PR (US)

(73) Assignee: University of Puerto Rico, San Juan Puerto Rico ( * ) Notice: Subject to any disclaimer, the term of this patent is extended or adjusted under 35 U.S.C. 154(b) by 105 days.

(21) Appl. No.: 13/439,813

(22) Filed: Apr. 4, 2012

Related U.S. Application Data (60) Provisional application No. 61/471,520, filed on Apr. 4, 2011.

(51) Int. Cl.
- *B22F 1/00* (2006.01)
- *B22F 9/00* (2006.01)
- *C22B 5/20* (2006.01)
- *C22B 11/00* (2006.01)
- *G01N 21/55* (2014.01)
- *B22F 9/24* (2006.01)

(52) U.S. Cl.
CPC ............... *G01N 21/554* (2013.01); *B22F 9/24* (2013.01)

USPC .............................................. 75/370; 75/741

(58) Field of Classification Search
USPC ....... 75/370, 371, 741; 977/773, 773 M, 840; 210/729
See application file for complete search history.

(56) References Cited

U.S. PATENT DOCUMENTS

| | | | |
|---|---|---|---|
| 7,212,284 B2 * | 5/2007 | Deng et al | 356/301 |
| 2011/0184202 A1 * | 7/2011 | Murphy et al. | 556/110 |

OTHER PUBLICATIONS

Shweta Hegde, Ridhima Chadha, Satyawati Joshi, Tulsi Mukherjee, Sudhir Kapoor Phase-transfer and size-dependent film formation of gold nanoparticles Materials Chemistry and Physics 118 (2009) 118-124.*

* cited by examiner

*Primary Examiner* — Roy King
*Assistant Examiner* — Jenny Wu
(74) *Attorney, Agent, or Firm* — Hoglund & Pamias, PSC; Roberto J. Rios (57) ABSTRACT

The invention described relates to the synthesis of gold nanorods in high concentrations in a single batch and their use in detection of nitroexplosives using Surface Enhanced Raman Spectroscopy (SERS). The nanoparticle suspensions were stable up to a month after preparation. The aggregated nanorods have a strong SERS effect for nitroexplosives (3,5-dintro-4-methylbenzoic acid and 2,4,6-TNT) with sensitivity of 5.0 pg in a few seconds. The results obtained in numerous tests demonstrated a high reproducibility that makes aggregated nanorods very attractive substrates for defense and security applications.

3 Claims, 7 Drawing Sheets

SURFACE ENHANCED RAMAN SPECTROSCOPY GOLD NANORODS SUBSTRATES FOR DETECTION OF 2,4,6-TRINITROTOULENE AND 3,5-DINITRO-4-METHYLBENZOIC ACID EXPLOSIVES

BACKGROUND OF THE INVENTION

The detection of explosives on different environments is of interest for Homeland Security and National Defense. In the last few years, Surface enhanced Raman scattering (SERS) has emerged as an important technique for the detection of biological and energetic materials due to its high sensitivity. SERS is a powerful spectroscopic technique for detecting low concentrations of analytes. Since its observation was first observed in 1974 and correctly explained in 1977 it has overcome the extremely low cross sections ($10^{-31}$ cm$^2$) of conventional Raman Spectroscopy by enhancing the typically low Raman intensity with factors of $10^6$ to $10^{14}$. The vibrational spectrum of a molecule displays a fingerprint map of the chemical composition of each chemical or biological agent. However the application of SERS for detecting nitroexplosives is still a challenging application to overcome due to the low affinity of these analytes to nanometallic surfaces. It was demonstrated that when the detection of 2,4,6-TNT was conducted with colloidal silver and gold in aqueous solutions a low limit of detection of $10^{-7}$ M could be achieved under optimum conditions. Gold, silver, and Au/Ag colloids synthesized by chemical reduction methods have also been used for detecting 2,4,6-TNT and 2,4-DNT in solution with high sensitivity and molecular specificity. In this application pH changes were needed to improve the detection. This proposed method has the problem that is an indirect detection which involves the alkaline hydrolysis of the explosives by causing the degradation of the explosives.

CTAB-gold nanoparticles have been used for other nitro explosives such as RDX with a wide nanometer size. Although the sensitivity of the nanoparticles was in the picogram range, the procedure needed the mixture of the colloidal suspension with the explosive before the deposition of them on a glass slide.

The detection of TNT, TATP and NG onto solid SERS substrates have been reported by depositing a gold layer on a silicon surface formed by microlithography. However, the sensitivity was in the range of 200-400 pg and high acquisition (signal integration) time had to be employed in the case of TNT (600 s).

A major problem related with the use of metal colloids is the tendency for colloidal aggregation after the addition of analytes, which makes the colloid unstable and leads often to poor reproducibility of the SERS spectra. To avoid variations in the SERS enhancement due to changes in colloid aggregation, a vast number of SERS investigations employ solid support-based substrates, such as metal island films and electrochemically roughened metals. Other techniques for nanostructure fabrication that can give better reproducibility than colloidal suspensions include electron beam lithography (EBL) and nanosphere lithography (NSL) provide fine control over interparticle spacing and can be used to generate nanostructures of different shapes. However, they constitute expensive and slow methods of preparation. Other shapes such as nanorods, nanowires and nanocubes are few of the reported shapes in the literature as SERS active substrates that have sharp surface features that produce vast localized field enhancements at the tips of the sharp features that make them attractive as good substrates for SERS applications. Gold-cetyl trimethylammonium bromide (CTAB) nanoparticles have been synthesized and used for the detection of 4-mercaptobenzoic acid on immobilized nanoparticles in a sandwich form in which the analyte is between a gold slide and the nanoparticles. This method works for analytes that can form a chemical bond with the gold slides and that can have an electrostatic interaction with CTAB-gold nanoparticles in the way to ease their attachment on it. The disadvantage of this method as a sensor for explosives is the fact that the nanoparticles are added to the gold slide after attaching the analyte and nitroexplosives are characterized for having poor affinity for the gold slide compared to sulfur compounds and the analysis would take a long time to be efficient in sensors applications. Also while trying to bind explosives to nanoparticle deposition at high solvent temperature would cause the evaporation of the nitroaromatic explosives from the solution due low water solubility and vapor pressure of many of these explosives.

The synthesis of gold nanorods is always accompanied by the formation of other shapes in the solution and their removal is a grand challenge. Platelets can be dissolved by adding Au(III)/CTAB complex to the nanorod final solution resulting in a conversion of platelets into smooth disk like structures, but the process takes hours for completion. A centrifugation protocol developed used to separate other shapes from nanorod solution is described which takes ~21 min.

What is needed is an inexpensive and versatile methodology of preparation, colloidal aggregation, high signal reproducibility (regarding SERS vibrational signals), sensitivity, applications to gas phase and while searching for sensing methodologies that would be able to detect nanomoles to femtomoles of high explosives on solid support SERS substrates.

SUMMARY OF THE INVENTION

According to an aspect of the invention, gold nanorods were synthesized in large scale under controlled temperature conditions and a narrow distribution of size of the final assembly at cyclohexane/water interface was achieved and tested in detection of 2,4,6-TNT and 3,5-dinitro-4-methylbenzoic.

According to another aspect, the invention is directed to the synthesis of gold nanorods in high concentrations in a single batch and their use in detection of nitroexplosives using Surface Enhanced Raman Spectroscopy (SERS).

In still another aspect of the invention, gold nanorods were synthesized using a seed-CTAB approach at well-controlled temperature in all the steps of the procedure.

According to a further aspect of the invention, the nanoparticle suspensions were stable up to a month after preparation with a small shift of the longitudinal plasmon (LP) around 623 nm. SERS activity decreased over time for all the characteristic bands at 390, 1077 and 1596 cm$^{-1}$ of the SERS probe molecule: 4-aminobenzenethiol (4-ABT).

In accordance to an aspect of the invention, gold nanorods were aggregated as films in cyclohexane/water interface using ethanol as an inducer. The experimental setup was very efficient for the preparation of the aggregated nanorods as films.

According to another aspect of the invention, results show that the aggregated nanorods have a strong SERS effect for nitroexplosives (3,5-dintro-4-methylbenzoic acid and 2,4,6-TNT) with sensitivity of 5.0 pg in a few seconds. The SERS activity found to be was closely dependent of the excitation laser wavelength.

According to still another aspect of the invention, the symmetric stretching vibration of the nitro group [$\upsilon_s(NO_2)$] at ~1345 cm$^{-1}$ and the asymmetric stretching vibration of the nitro group [$\upsilon_{as}(NO_2)$] at ~1571 cm$^{-1}$ were clearly observed. The results obtained in numerous tests demonstrated a high reproducibility that makes aggregated nanorods very attractive substrates for defense and security applications.

BRIEF DESCRIPTION OF THE DRAWINGS

Further features and advantages of the invention will become apparent from the following detailed description taken in conjunction with the accompanying figures showing illustrative embodiments of the invention, in which.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

Synthesis of Gold Nanorods

Gold nanorods (GNRs) were prepared in large scale by performing modifications of a protocol reported before. The synthesis begins with the preparation of a seed colloidal suspension. First 250 μL of an aqueous 0.01 M solution of HAuCl$_4$.3H$_2$O are added to 7.5 mL of 0.1 M CTAB solution in a 50 mL plastic centrifuge tube and mixed gently. Then, 600 μL of an aqueous ice-cold solution of 0.01 M NaBH$_4$ is added. By moderately mixing for 2 min, the solution turns to a pale-brown yellow color. The solution is maintained undisturbed for 2 h at 25° C. for further GNRs growth. The solution has to be heated to 27° C. since CTAB has poor water solubility.

A 45.2 mL batch of nanorods colloidal suspensions is prepared as follows: 270 μL of 0.01 M AgNO$_3$ water solution is added to 42.75 mL CTAB solution in a 50 mL plastic centrifuge tube followed by addition of 1.8 mL of 0.01 M HAuCl$_4$3H$_2$O aqueous solution. They are then gently mixed after addition of the silver and gold solutions to the CTAB solution. Then, a 0.1 M ascorbic acid aqueous solution (288 μL) is added to the mixture (the solution becomes colorless). Finally, the seed solution is added (90 μL), and the reaction tube is maintained undisturbed for 12 hr at 27° C. At the end of the procedure the solution turns blue.

Figure 1:
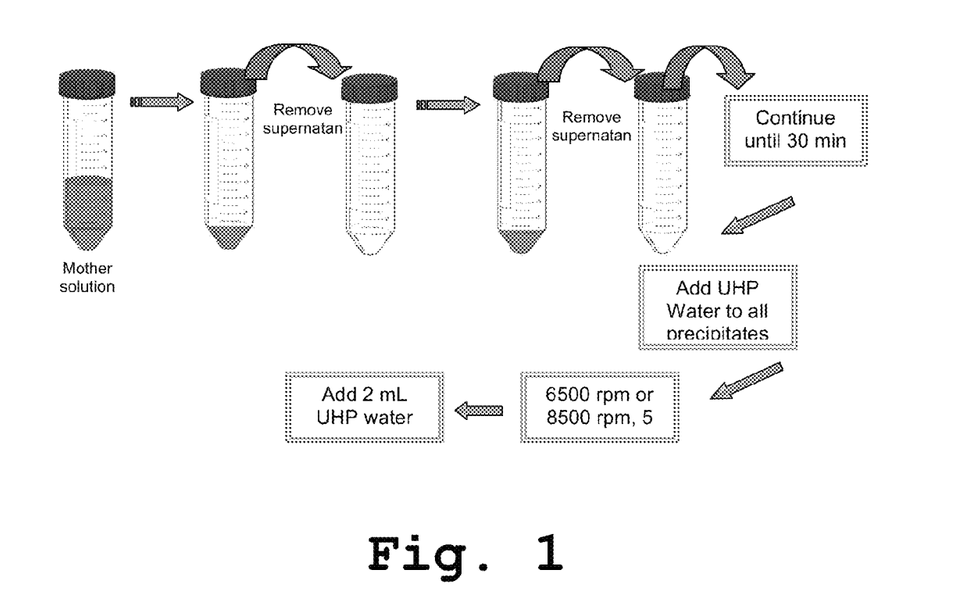
FIG. 1 illustrates the details of the centrifugation process according to the present invention.

Significant time was dedicated to study the procedure to separate nanorods from spheres and other shapes by centrifugation of nanorods solutions. Two different centrifugation speeds were tested: 6,500 and 8,500 rpm, removing the surfactant and transferring to another test tube every 3-5 minutes. The details of the centrifugation process are illustrated in FIG. 1. The absorbance and plasmon locations obtained by ultraviolet-visible (UV-Vis) light absorption spectrophotometry were used for determining nanoparticle concentration according to previously reported extinction coefficients. The same procedure was followed for four months in order to analyze the GNRs stability over time. GNRs were kept at 8° C. for further analysis.

SERS Experiments in Solution

Figure 2:
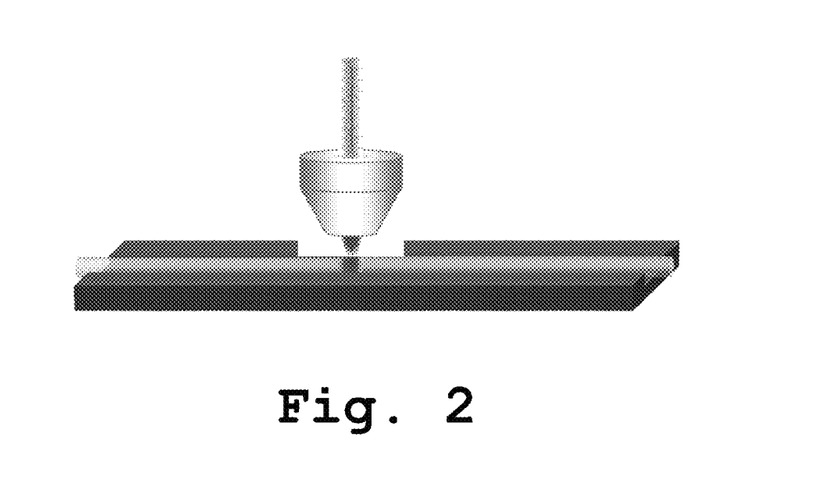
FIG. 2 illustrates a custom-made stainless steel holder designed for running the SERS experiments according to present invention.

SERS probe molecule was 4-aminobenzethiol (4-ABT). A custom-made stainless steel holder was designed for running the SERS experiments as illustrated in FIG. 2. The holder has a circular cutoff along its center in which the capillary tube is placed. This holder the capillary tube rigidly and reproducibly while running the experiments The final concentration on the NR solution was 1 μM for excitation wavelength effects and nanoparticle dilution studies. The sensitivity of the GNRs was characterized by measuring SERS spectra while decreasing 4-ABT molar concentrations. GNRs and 4-ABT were mixed with hand agitation and SERS spectra were obtained 5 min after sample preparation to ensure that the analyte was adsorbed on the nanoparticles. A small volume of this sample was transferred to a glass capillary tube (1.5×90 mm) and placed in the stainless steel capillary tube holder fused for SERS and Raman experiments under microscope or macro experiments.

Self Assembling of Gold Nanorods at Cyclohexane/Water Interface

Figure 3:
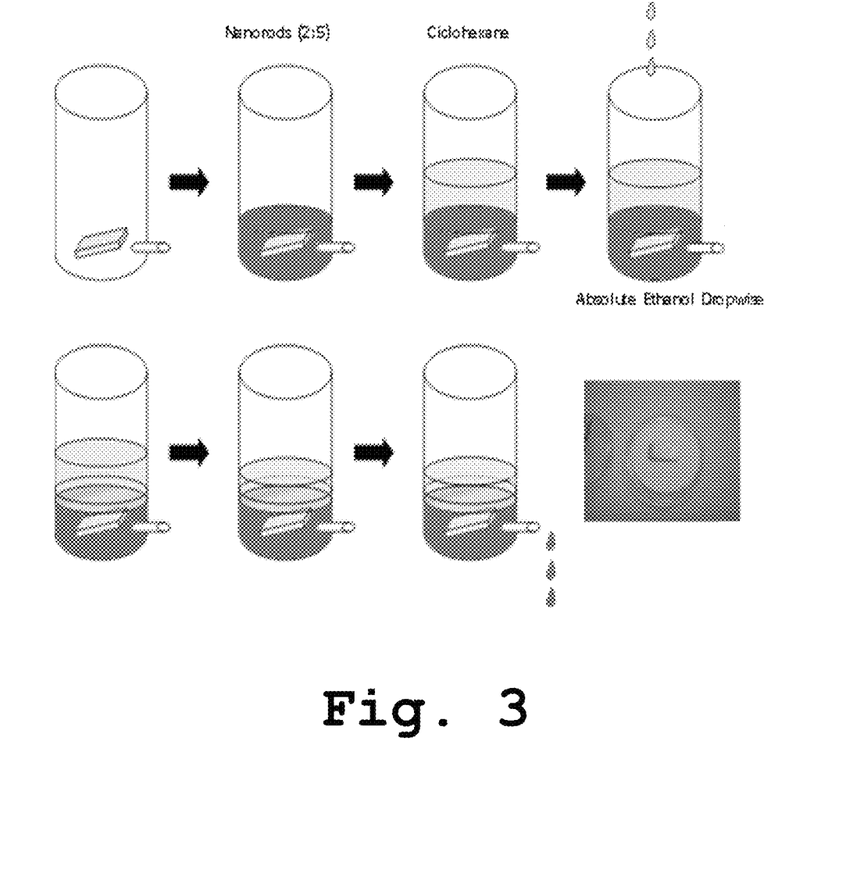
FIG. 3 illustrates the self-assembling of gold nanorods at cyclohexane/water interface according to the present invention.

Two milliliters of the original nanorods solution were mixed with three milliliters of water and were transferred to a glass beaker as illustrated in FIG. 3. Two milliliters of cyclohexane were added to the top of the nanorod solution forming an immiscible water/cyclohexane interface. Then, absolute ethanol (2 mL) was added dropwise to the solution using a Pasteur pipette, leading to the nanorod film to be trapped at the cyclohexane/water interface.

Ethanol helps to remove all the excess of surfactant and to acts as an inducer. Then, part of the cyclohexane (bottom phase) was removed and drained out the solution until the bottom of the beaker containing the Au/glass slide (1 cm×1 cm or 1 cm×2 cm) was completely covered with the nanoparticles as shown at the end of FIG. 3.

Explosives SERS Experiments

SERS spectra from the aggregated nanorods were recorded after 24 hr of the film preparation to ensure the evaporation of the cyclohexane. 2,4,6-TNT was dissolved in absolute ethanol. 3,5-DN-4-M-BA was prepared in water and the pH was changed to 9.0 to guarantee the proton dissociation. Five micro liters of the sample solutions were spread out on the SERS substrates and 10 min of incubation were waited before running SERS experiments to facilitate the adsorption of the analytes on the substrates.

Results:

The invention is based on the use of gold nanorods as SERS substrate for detecting nitroexplosives. One of the main aspects of the invention is to guarantee that the vast majority of the nanoparticles (NPs) present in the colloidal suspension ensemble were rods. An inspection of the intensity distribution of the longitudinal (LP) and transverse (TP) plasmons in the UV-Vis spectra provided important findings about the population of NPs. Namely, that the nanorods have different location of both plasmon components and that the two components vary in relative intensity. The transverse plasmon has contributions from nanorods and from spheres present in the suspension. The longitudinal plasmon is due only to the presence of nanorods. The ratio of intensities of both plasmons was obtained to determine the effect of speed and time of centrifugation on the separation of spheres and separation of nanorods of different sizes. For example, intensity ratios for 3 min and 15 min were 1.83 and 2.15, respectively.

Figure 4:
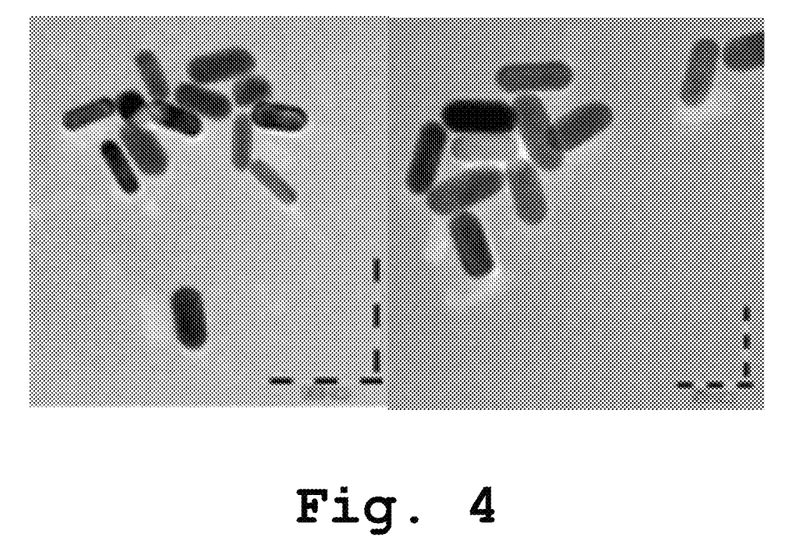
FIG. 4 shows TEM images of nanorods with different shapes according to the present invention.

From the methods of centrifugation it can be concluded that by using a speed of 6500 rpm for 15 min is an efficient method to separate different shapes from the nanorods achieving an 85% of spheres separation. These results were confirmed by TEM images as the ones shown in FIG. 4, centrifuged at 6,500 rpm: (a) 3 min centrifugation, scale: 100 nm; (b) 15 min centrifugation, scale: 50 nm. By comparing the TEM images only nanorods were obtained at this centrifuging speed and the aspect ratio obtained was ~2.

Table 1 below summarizes how the concentration of GNRs changes with different batches using the same reagents. It is clearly observed that there is a variation on the concentration of ±0.2 nM. This can be attributed to some sample loss during centrifugation process while the supernatant is removed from the rods.

TABLE 1

| GNR* | [nM] |
|---|---|
| $B_O$ | 1.28 |
| $B_P$ | 1.35 |
| $B_Q$ | 1.72 |
| $B_R$ | 1.58 |
| $B_S$ | 1.31 |
| $B_T$ | 1.56 |
| $B_X$ | 1.68 |

*From $B_O$ to $B_X$ represent nanorods from different batches.

Stability of the GNRs

Figure 5:
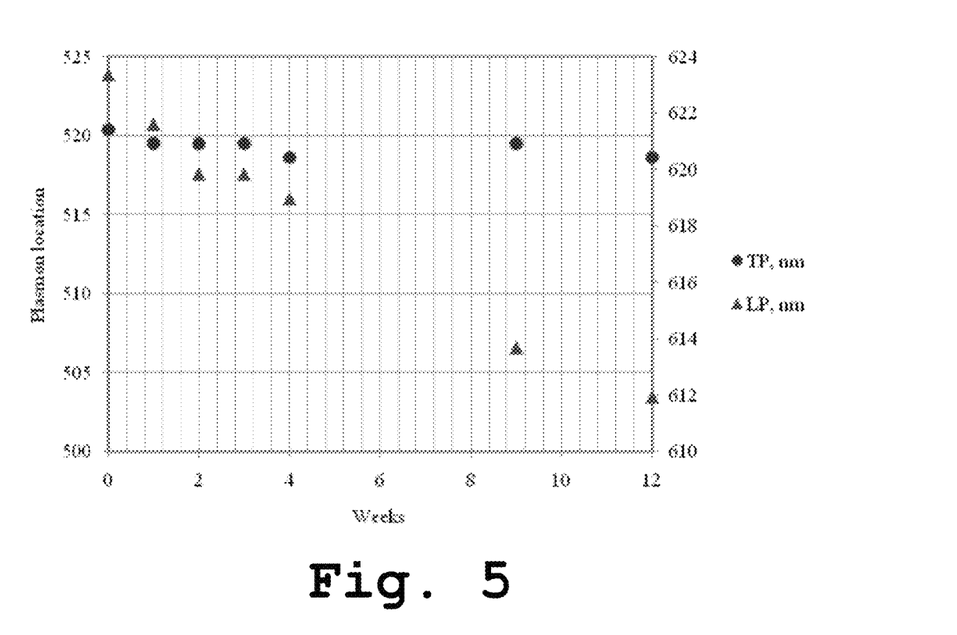
FIG. 5 shows a plot of the variation of the wavelength location of TP and LP components of GNRs according to the present invention.

When the idea to propose the synthesized gold nanorods as a sensor for explosives detection using SERS was conceived, one of the main aims of the invention was to study the stability of the GNR over a long period of time (more than 30 days). FIG. 5 shows a plot of the variation of the wavelength location of TP and LP components of GNRs with the time up to week 12 (three months). The synthesized GNRs were aged for three months at 8° C. instead of room temperature.

According to the intensity of LP and TP it can be concluded that both NRs plasmons change in location and intensity over time. TP values were approximately 0.17 in absorbance units. The location of TP changed only 2 nm from week zero to week 12. However, values of LP locations changed drastically in 12 nm. The LP component band position moved significantly from 623.4 nm to 612 nm in three months. Since the LP component band is related with the length of the GNR, the results presented indicate that the length of the nanorods decreases with aging time. Just the contrary happens to the width that is not significantly affected with aging time. An explanation of this fact is due the atomic defects on the {110} facets on the GNRs.

Figure 6:
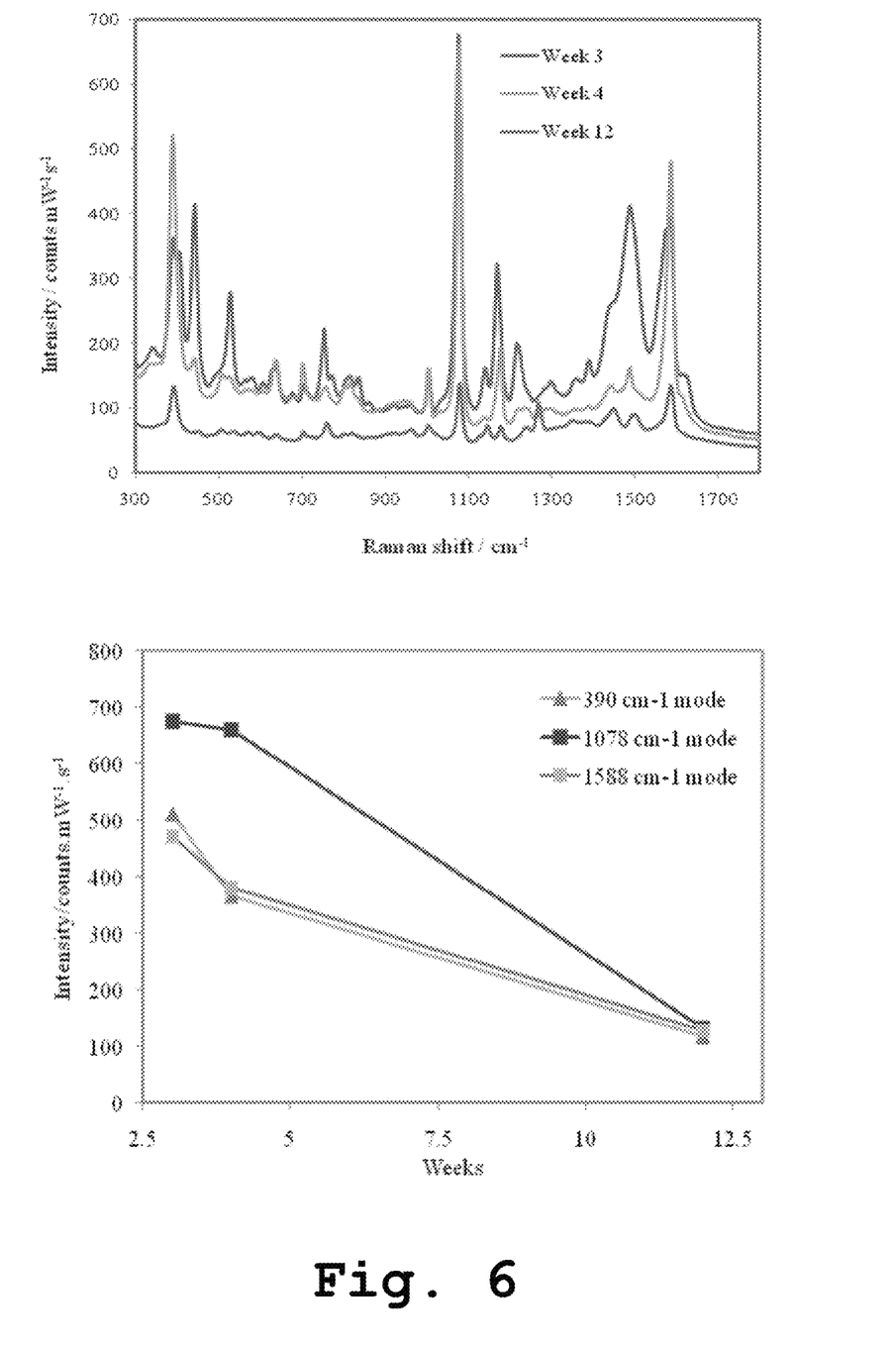
FIG. 6 shows SERS spectra of 4-ABT and SERS activity of the GNR at several intervals of time according to the present invention.

SERS activity of the GNR prepared was analyzed at the beginning and the end of the aging period. According to FIG. 6, (a) SERS spectra of 4-ABT at week 3, 4 and 12 measured using 785 nm excitation line; (b) SERS activity of the GNR at several weeks after preparation), there is a gradual decrease in intensity of the bands located at 390, 1078 and 1588 cm$^{-1}$ with time. There is no large loss of SERS activity in 4 weeks. However, after 12 weeks the signals decrease by 90% compared with freshly prepared nanoparticles. These results confirm that SERS signal depends on the nanoparticle aging.

Assembling of Gold Nanorods

The system for assembling GNRs consists of a platform in which the slide is on an angle of inclination of 5° to 10° inside a capped glass vessel, which also has a system to drain the solution. The slide is placed inside before adding the corresponding amounts of cyclohexane, nanorods solution and ethanol. Once the system achieved the conditions in which the nanoparticles were enclosed in the organic-aqueous interface forming the sought films, the system was allowed to drain, which led to the appearance of a mirror like metallic shine due the result of optical coupling of the gold nanorods.

Figure 7:
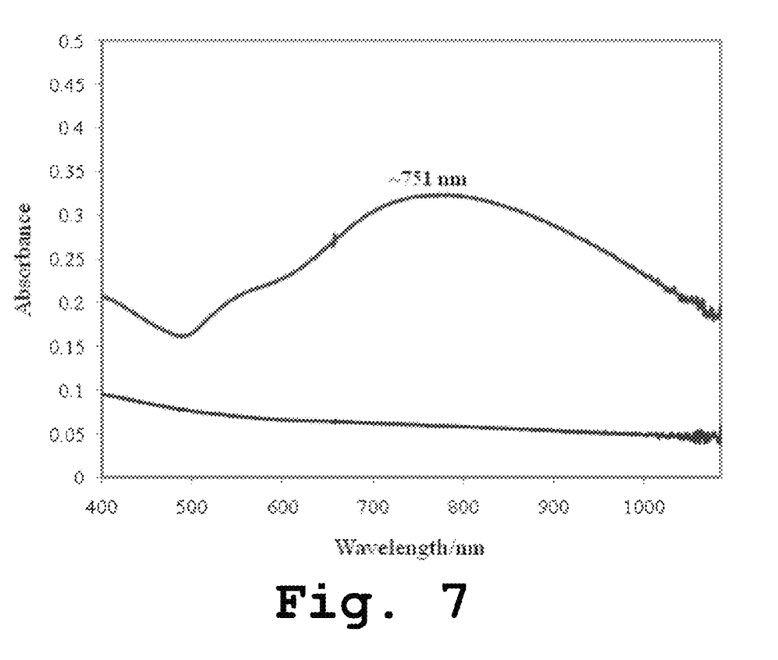
FIG. 7 shows a plot demonstrating that when the spacing between nanorods deposited reaches a maximum value; the surface plasmon modes began to interact to give rise to a wide band according to the present invention.

When the spacing between nanorods deposited reaches a maximum value, the surface plasmon modes began to interact to give rise to a wide band as shown in FIG. 7 (a) Red: Aggregated GNRs; (b) gray: Au—Si slide. The maximum peak is located ca ~751 nm which is close to the 785 nm excitation line. The gray line in the graph is the spectrum on the slide without any nanorods. This broad plasmon band is attractive for exploring excitation with various laser wavelengths.

Figure 8:
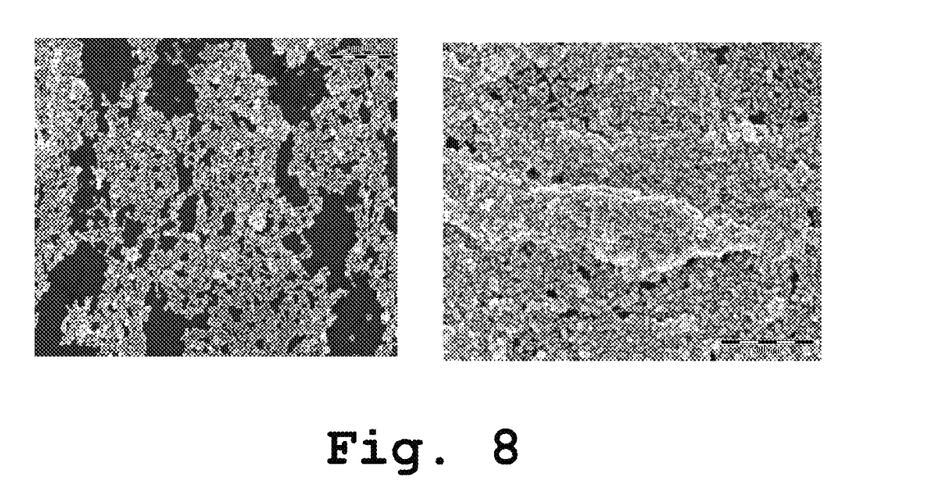
FIG. 8 shows representative field emission-scanning electron microscope (FE-SEM) images of the aggregated gold nanorods according to the present invention.

FIG. 8 shows representative field emission-scanning electron microscope (FE-SEM) images of the aggregated gold nanorods (a) and (b, high magnification). According to these images, large area is covered for the nanorods with a high density on the substrate. GNRs are closely packed (high magnification, FIG. 8) on the entire surface with high coverage with the exception of some areas that are not covered by the nanorods. In addition, the procedure with cyclohexane gave the formation of multilayers organized in three-dimensional arrays with some void spaces. The poor distance definition between nanoparticles increased the optical coupling since more GNRs are in contact with each other causing the presence of a broad plasmon band. The presence of large void spaces on the film can be attributed to high water draining speed during solvent separation.

SERS Experiments with Explosives

Figure 9:
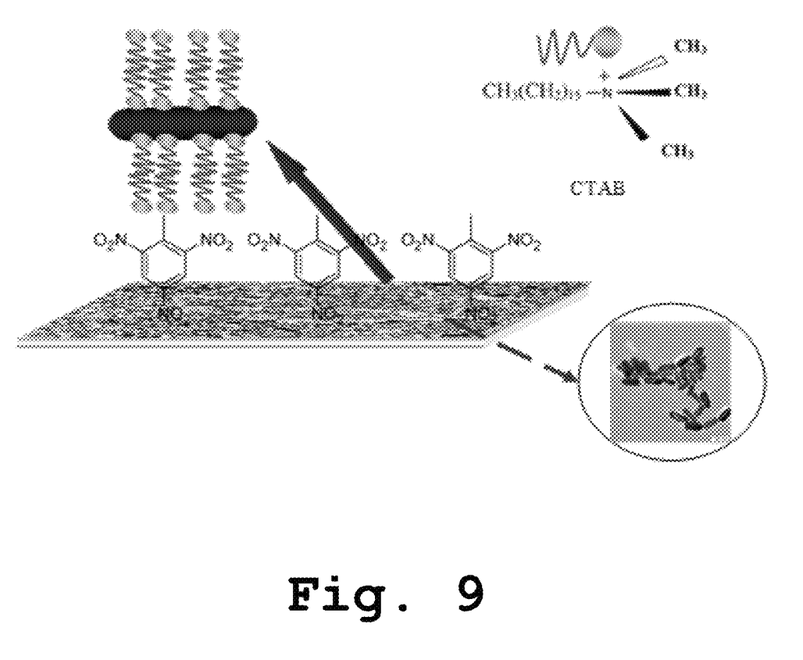
FIG. 9 illustrates the SERS sensor using gold nanorods according to the present invention.

The described SERS sensor in this invention using gold nanorods is depicted in FIG. 9. Although the presence of the broad plasmon band on the aggregated nanorods allows the use of a wide range of excitation lines, experiments were only performed at 785 nm. The idea was to induce an electromagnetic enhancement with the laser line close to the maximum plasmon band located at the junction of the nanorods due to hot spots formed. The plan was to have the maximum enhancement with a fine control of gap between NPs having explosives molecules adsorbed on hot spots.

Figure 10:
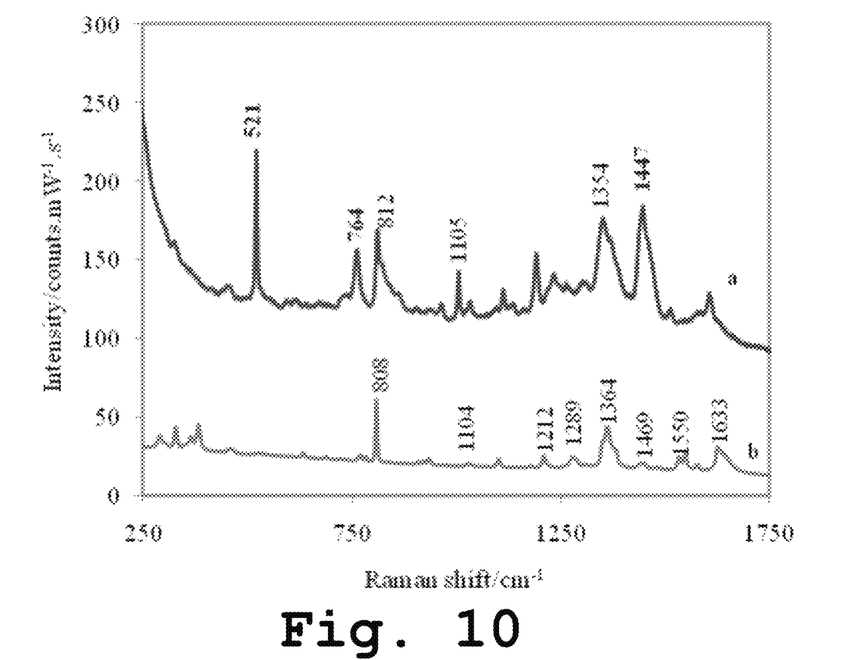
FIG. 10 shows normal Raman spectrum and SERS spectrum of 3,5-dinitro-4-methyl-benzoic acid and SERS spectrum and normal Raman of 3,5-D-4-M-BA adsorbed on GNRs according to the present invention.

The normal Raman spectrum and SERS spectrum of 3,5-dinitro-4-methyl-benzoic acid is depicted in FIG. 10, (a) SERS spectrum (red trace); and (b) normal Raman of 3,5-D-4-M-BA adsorbed on GNRs (blue trace). Spectra were normalized to acquisition time and laser power ($\lambda_{exc}$=785 nm). The bands labeled in bold in the SERS spectrum are due the CTAB micelles and correspond to $CH_3$ deformation mode 1447 cm$^{-1}$ and the C—N+ stretching mode at 764 cm$^{-1}$. The change in intensity of some bands is clearly observed and according to the surface selection rules it can give information related to the orientation of the nitrocompound on the surface. The 1024 cm$^{-1}$ ring in-plane deformation and C—C symmetric stretch is very weak in the normal Raman spectrum, but it increases in the SERS spectrum. In the same way, the nitro vibration at 1364 cm$^{-1}$ undergoes 10 cm$^{-1}$ shift. Such spectral changes suggest that the molecule is adsorbed on the gold nanorod surface with the nitro groups near the surface and the aromatic ring is perpendicular to the surface. The band at 521 cm$^{-1}$ is attributed to the Si surface signal.

Figure 11:
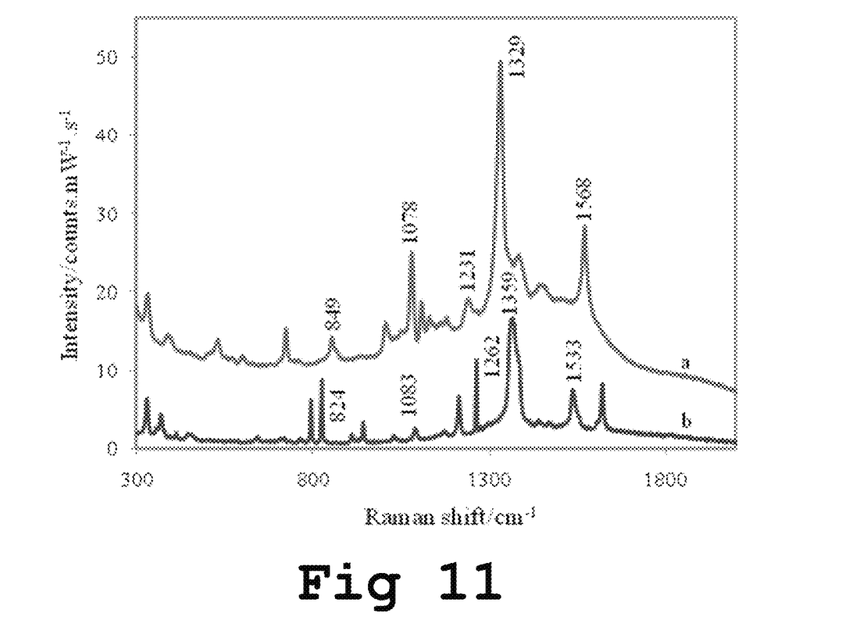
FIG. 11 shows SERS and normal Raman spectrum of 2,4,6-TNT and SERS spectrum and normal Raman spectrum of 2,4,6-TNT adsorbed on GNR according to the present invention.

The way 2,4,6-TNT can be oriented on nanometallic surfaces of colloidal suspensions has been discussed by Kneipp with the molecule oriented perpendicular to the nanoparticle surface. SERS and normal Raman spectrum of 2,4,6-TNT is shown in FIG. 11, (a) SERS spectrum (blue trace); and (b) normal Raman spectrum (red trace) of 2,4,6-TNT adsorbed on GNR. Spectra are normalized to acquisition time and laser power ($v_{exc}$=785 nm). The increase in intensity of the band at 1078 cm$^{-1}$ (ring breathing mode) in the SERS spectrum is clearly observed. Comparing the SERS spectrum with the normal one, this vibration is very weak. The moderately strong enhancement of this vibrational mode in the SERS spectrum suggests that TNT molecules on nanorods are oriented perpendicular to the surface. In addition, the symmetric stretching vibration of the nitro group [$v_s(NO_2)$] at 1359 cm$^{-1}$ and the asymmetric stretching vibration of the nitro group [$v_{as}(NO_2)$] at 1533 cm$^{-1}$ undergo considerable shifts, indicating that the nitro groups are located near the GNR surface.

By considering the $4.5\times10^{-5}$ cm$^2$ laser spot and 10× objective it was possible to detect 10.2 pg of 2,4,6-TNT and 5.0 pg of 3,5-DN-4-M-BA. As seen in Table 2 below, the numbers of molecules/cm$^2$ are $2.7\times10^{10}$ and $1.4\times10^{10}$ for 2,4,6-TNT and 3,5-DN-4-M-BA, respectively. The sensitivity is comparable with previous studies that detected picogram amounts of TNT under 150 μm spot laser.

The nitro symmetric band was used to perform reproducibility studies. Five spectra were recorded at different locations on the substrates to test for reproducibility on the formation of the film prepared using cyclohexane/water interface. Taking into account peak areas a 5% variation coefficient was determined, indicating very good reproducibility. This demonstrates that nanorods deposited using cyclohexane/water interface aggregated almost homogenously on the glass slide. This self-assembly method can be used for further nanoparticles and SERS studies.

TABLE 2

| Nitro-compound | MW (g/mol) | Laser spot (cm$^2$) | g/cm$^2$ | pg/cm$^2$ | molecules/cm$^2$ |
|---|---|---|---|---|---|
| 2,4,6-TNT | 227.1 | $4.5\times10^{-5}$ | $1.0\times10^{-11}$ | 10.2 | $2.7\times10^7$ |
| 3,5-DN-4-M-BA | 226.1 | $4.5\times10^{-5}$ | $5.1\times10^{-12}$ | 5.1 | $1.4\times10^{10}$ |

Laser; 785 nm, objective: 10×

CTAB-seed mediated gold nanorods promise to be good sensing platforms for SERS in trace detection of nitroexplosives. The sensitivity of the GNRs was in the range of 5-10 pg under the laser spot. This sensitivity is comparable with other studies reported in the literature. However, the use of other excitation lines is really needed to explore the effect on the enhancements. Also, the GNR/water ratio for assembling must be explored to see the effects on the nanorods gaps. The setup used to prepare the films of nanorods on cyclohexane/water interface and transfer to a solid substrate was very efficient for the preparation of the aggregated nanorods as films. Apparently, a large surface area was covered by the GNR. The amount of ethanol was found to be critical for the formation of the nanorods films at the cyclohexane/water interface. The two dimensional arrangement of the nanorods will possibly allow the control of the gap distance between nanoparticle and increase the sensitivity.

To the best of our knowledge, the gold nanoparticles of the invention have not been reported as SERS substrates used as sensors for explosives detection. Nanorods described in this invention have the suitable size to be used as SERS substrates (ranging from 60 to 120 nm, average lengths) compared to commercially available gold spherical nanoparticles (average length: 45 to 60 nm. The proposed colloidal suspensions are stable for three months which offer advantages for commercialization. The nanoparticles described in this invention were produced in large scale with a good reproducibility in the synthesis on several independent batch processes.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A method of fabricating surface enhanced Raman Spectroscopy gold nanorods comprising:
    synthesizing gold nanorods using a seed cetyl cetyl trimethylammonium bromide (CTAB) technique; and
    aggregating said gold nanorods as films in a cyclohexane/water interface using an inducer by:
        a) mixing a gold nanorod solution with water and transferring said mixed gold nanorod solution with water into a beaker having a glass slide positioned on an angle of inclination of about 5° to about 10°;
        b) adding cyclohexane to the top of said gold nanorod solution forming an immiscible water/cyclohexane interface;
        c) adding ethanol leading to said gold nanorod film to be trapped at the water/cyclohexane interface; and
        d) removing part of said cyclohexane and draining out the gold nanorod solution leaving the glass slide covered with gold nanoparticles.

2. The method of claim 1, wherein said gold nanorods are synthesized by:
    e) add and mix an aqueous solution of HAuCl$_4$.3H$_2$O to a CTAB solution;
    f) add to said mixture of step e) an aqueous ice-cold solution of NaBH$_4$ to form a first mixture;
    g) separately add and mix a AgNO$_3$ water solution to CTAB solution followed by adding an HAuCl$_4$.3H$_2$O aqueous solution;
    h) add ascorbic acid aqueous solution and the first mixture to said separate mixture of step g).

3. The method of claim 2, wherein nanorods are separated from spheres and other shapes by centrifugation of nanorods solutions.

* * * * *